US005635345A

United States Patent [19]

Scherrer et al.

[11] Patent Number: 5,635,345

[45] Date of Patent: Jun. 3, 1997

[54] METHOD FOR THE DIAGNOSIS OF HIV USING ANTIBODIES TO PROSOMES

[75] Inventors: Klaus Scherrer, Paris; Jean P. Bureau, Castelnau le Nez; Faycal Bey, Paris, all of France

[73] Assignee: Akzo Nobel N.V., Arnhem, Netherlands

[21] Appl. No.: 202,857

[22] Filed: Feb. 25, 1994

Related U.S. Application Data

[63] Continuation of Ser. No. 860,492, filed as PCT/EP91/01945, Oct. 10, 1991 published as WO92/07269, Apr. 30, 1992, abandoned.

[30] Foreign Application Priority Data

Oct. 11, 1990 [EP] European Pat. Off. ............. 90402838

[51] Int. Cl.$^6$ .................................................. C12Q 1/70
[52] U.S. Cl. .................. 435/5; 435/7.1; 435/7.2; 435/7.24; 435/7.4; 435/7.92; 435/974; 435/975; 530/350
[58] Field of Search ................... 435/5, 7.1, 7.2, 435/7.4, 974, 975, 7.24, 7.92; 530/350

[56] References Cited

U.S. PATENT DOCUMENTS 5,059,521 10/1991 Scherrer .

FOREIGN PATENT DOCUMENTS 0219368 4/1987 European Pat. Off. .
0345750 12/1989 European Pat. Off. .

OTHER PUBLICATIONS

Research Reagent News, vol. 1, Jan. 1, 1991, "Anti–prosomal Mouse monoclonal antibodies," pp. 1–4, published by Organon Teknika, N.V.

*Primary Examiner*—Christine M. Nucker
*Assistant Examiner*—Jeffrey Stucker
*Attorney, Agent, or Firm*—Mary E. Gormley

[57] ABSTRACT

This invention is directed to a method useful in the diagnosis of HIV. The method involves reacting monoclonal antibodies to particular prosomal proteins with certain blood cell types obtained from a sample, and observing an increase or decrease in the levels of the prosomal proteins on the cell's surface.

6 Claims, 7 Drawing Sheets

```
CGG TGC CTG GTG CGG GAG CTA CGG GGC CCA GGG ATT GTG TTT AAA GTA    48
    Cys Leu Val Arg Glu Leu Arg Gly Pro Gly Ile Val Phe Lys Val
    1               5                   10                  15

GTG CTT CTA CCA ACA TGT CCC GTG GTT CCA GCG TTG ACC GCC            96
Val Leu Leu Pro Thr Cys Pro Val Val Pro Ala Leu Thr Ala
                20                  25                  30

ACA TTA CCA TTT TCA CCC GAG GGT CGG CTC TAC CAA GTA GAA TAT       144
Thr Leu Pro Phe Ser Pro Glu Gly Arg Leu Tyr Gln Val Glu Tyr
            35                  40                  45

GCT TTT AAG ATT AAC CAG GGT GGC CTT ACA TCA GTA GCT GTC AGA       192
Ala Phe Lys Ile Asn Gln Gly Gly Leu Thr Ser Val Ala Val Arg
        50                  55                  60

GGA AAA GAC TGT GCA GTA ATT GTC ACA CAG AAG AAA GTA CCT GAC AAA   240
Gly Lys Asp Cys Ala Val Ile Val Thr Gln Lys Lys Val Pro Asp Lys
            65                  70                  75

TTA GAT TCC AGC ACA ACT CAC TTA TTC AAG ATA ACT GAA AAC           288
Leu Asp Ser Ser Thr Thr His Leu Phe Lys Ile Thr Glu Asn
80                  85                  90          95

ATT GGT TGT GTG ATG ACC GGA ATG ACA CCT GAC AGC AGA TCC CAG GTA   336
Ile Gly Cys Val Met Thr Gly Met Thr Ala Asp Ser Arg Ser Gln Val
                100                 105                 110

CAG AGG GCA CGC TAT GAG GCA GCT AAC TGG AAA TAC AAG TAT GGC TAT   384
Gln Arg Ala Arg Tyr Glu Ala Ala Asn Trp Lys Tyr Lys Tyr Gly Tyr
        115                 120                 125

GAG ATT CCT GTG GAC ATG CTG TGT AAA AGA ATT GCC GAT ATT TCT CAG   432
Glu Ile Pro Val Asp Met Leu Cys Lys Arg Ile Ala Asp Ile Ser Gln
            130                 135                 140
```

```
GTC TAC ACA CAG AAT GCT GAA ATG AGG CCT CTT GGT TGT TGT ATG ATT       480
Val Tyr Thr Gln Asn Ala Glu Met Arg Pro Leu Gly Cys Cys Met Ile
    145                 150                 155

TTA ATT GGT ATA GAT GAA GAG CAA GGC CCT CAG GTA TAT AAG TGT GAT       528
Leu Ile Gly Ile Asp Glu Glu Gln Gly Pro Gln Val Tyr Lys Cys Asp
160                 165                 170                 175

CCT GCA GGT TAC TAC TGT GGG TTT AAA GCC ACT GCA GCG GGA GTT AAA       576
Pro Ala Gly Tyr Tyr Cys Gly Phe Lys Ala Thr Ala Ala Gly Val Lys
                180                 185                 190

CAA ACT GAG TCA ACC AGC TTC CTT GAA AAA GTG AAG AAA TGC CTG TCT       624
Gln Thr Glu Ser Thr Ser Phe Leu Glu Lys Val Lys Lys Cys Leu Ser
            195                 200                 205

GAT TGG ACA TTT GAA CAG ACA GTG GAA ACT GCA ATT ACA GAA GTT GGA GTA   672
Asp Trp Thr Phe Glu Gln Thr Val Glu Thr Ala Ile Thr Glu Val Gly Val
        210                 215                 220

ACT GTT CTA TCA ATT GAT TTC AAA CCT TCA GAA ATA CTT ACA GAA GCA GAG ATT  720
Thr Val Leu Ser Ile Asp Phe Lys Pro Ser Glu Ile Leu Thr Glu Ala Glu Ile
    225                 230                 235                 250   255

GTG ACA GTT GAA AAT CCT AAA CCT AAG CCT AAT CCT AGG ATT CTT ACA GAA GCA GAG ATT  768
Val Thr Val Glu Asn Pro Lys Pro Lys Pro Asn Pro Arg Ile Leu Thr Glu Ala Glu Ile
240                 245                 250                 255

GAT GCT CAC CTT GTT GCT CTA GCA GAG AGA GAC TAAACATTGT CGTTAGTTTA       821
Asp Ala His Leu Val Ala Leu Ala Glu Arg Asp
                260                 265

CCAGATCCGT GATGCCACTT ACCTGTGTGT TTGGTAACAA CAAACAAACA TCATGGAGGT       881

CCCTGGATTG AAAAAGGAGC CTCTCCCACT CCTCCTACCA CCGAAGTGGT TAGGACTCTA       941

TATAAATAAA AACAAGGCTT TTGGAAAAAA AAAAAAAA                               980
```

FIG. 9B

```
CGCGAGCCGGGACCACGCCGACCCAGCGTGCCCAGGCCGAGGAAAGCGCGGCGGCGGCAGTCCGAAGACCCA      72
CCGGACTGAAAGAGAAGGACGAGGTCATCTTCGGACGGGAGGGGCAAGCCAGCCATCCTGGGACCCCAGGCG     144
TGCAGGTTCTCTTTGAGGGTATTCCACCCTGCAAAAAGCATGTATTCATGGTCAGCTCTCAGCAAGGCCAGT     216
AGCAGAGTGGTAAAGGCCTTGGCCCTCCAAGGCTGGGAAAAGACAATGACAAGTCAAATCCAGACCTATGTT     288
GGATGTTGGTCTACTAGGTGACTGTCTCCTGGAAATGTT ATG CAG CTC AGC AAG GTG AAG TTT      351
                                         M   Q   L   S   K   V   K   F        8
CGA AAT CAG TAT GAC AAT GAT GTC ACT GTT TGG ACC GCC CAG GGC AGG ATT CAT      405
 R   N   Q   Y   D   N   D   V   T   V   W   T   A   Q   G   R   I   H        26
CAA ATT GAA TAT GCA ATG GAA GCT GTT AAA CAA GGT TCA GCC ACA GTT GGT CTG      459
 Q   I   E   Y   A   M   E   A   V   K   Q   G   S   A   T   V   G   L        44
AAA TCA AAA ACT CAT GCA GTT TTG GTT GCA TTG AAA AGG GCG CAA TCA GAG CTT      513
 K   S   K   T   H   A   V   L   V   A   L   K   R   A   Q   S   E   L        62
GCA GCT CAT CAG AAA AAA ATT CTC CAT GTT GAC AAC CAT ATT GGT ATC TCA ATT      567
 A   A   H   Q   K   K   I   L   H   V   D   N   H   I   G   I   S   I        80
GCG GGG CTT ACT GCT GAT GCT AGA CTG TTA TGT AAT TTT ATG CGT CAG GAG TGT      621
 A   G   L   T   A   D   A   R   L   L   C   N   F   M   R   Q   E   C        98
TTG GAT TCC AGA TTT GTA TTC GAT AGA CCA CTG CCT GTG TCT CGT CTT GTA TCT      675
 L   D   S   R   F   V   F   D   R   P   L   P   V   S   R   L   V   S       116
CTA ATT GGA AGC AAG ACC CAG ATA CCA ACA CAA CGA TAT GGC CGG AGA CCA TAT      729
 L   I   G   S   K   T   Q   I   P   T   Q   R   Y   G   R   R   P   Y       134
GGT GTT GGT CTC CTT ATT GCT GGT TAT GAT GAT ATG GGC CCT CAC ATT TTC CAA      783
 G   V   G   L   L   I   A   G   Y   D   D   M   G   P   H   I   F   Q       152
ACC TGT CCA TCT GCT AAC TAT TTT GAC TGC AGA GCC ATG TCC ATT GGA GCC CGT      837
 T   C   P   S   A   N   Y   F   D   C   R   A   M   S   I   G   A   R       170
TCC CAA TCA GCT CGT ACT TAC TTG GAG AGA CAT ATG TCT GAA TTT ATG GAG TGT      891
 S   Q   S   A   R   T   Y   L   E   R   H   M   S   E   F   M   E   C       188
AAT TTA AAT GAA CTA GTT AAA CAT GGT CTG CGT GCC TTA AGA GAG ACG CTT CCT      945
 N   L   N   E   L   V   K   H   G   L   R   A   L   R   E   T   L   P       206
GCA GAA CAG GAC CTG ACT ACA AAG AAT GTT TCC ATT GGA ATT GTT GGT AAA GAC      999
 A   E   Q   D   L   T   T   K   N   V   S   I   G   I   V   G   K   D       224
TTG GAG TTT ACA ATC TAT GAT GAT GAT GAT GTG TCT CCA TTC CTG GAA GGT CTT     1053
 L   E   F   T   I   Y   D   D   D   D   V   S   P   F   L   E   G   L       242
GAA GAA AGA CCA CAG AGA AAG GCA CAG CCT GCT CAA CCT GCT GAT GAA CCT GCA     1107
 E   E   R   P   Q   R   K   A   Q   P   A   Q   P   A   D   E   P   A       260
GAA AAG GCT GAT GAA CCA ATG GAA CAT TAA GTGATAAGCCAGTCTATATATGTATTATCAA     1168
 E   K   A   D   E   P   M   E   H   *                                       270
ATATGTAAGAATACAGGCACCACATACTGATGACAATAATCTATAGTTTAACCAAAAGTTGCAGAGTGGTGG    1240
AATGCTATTTTTTAGGAATCAGTC                                                    1264
```

FIG. 10

METHOD FOR THE DIAGNOSIS OF HIV USING ANTIBODIES TO PROSOMES

This is a continuation of U.S. Ser. No. 07/860,492, filed Aug. 11, 1992, now abandoned, which is a 35 USC 171 continuation of PCT EP91/01945, Oct. 10, 1991 published as WO92/07269, Apr. 30, 1992.

TECHNICAL FIELD

This invention relates to diagnostic methods useful in the diagnosis of HIV infection.

BACKGROUND ART

Acquired immune deficiency syndrome ("AIDS") is a disease thought most likely to be caused by the human immunodeficiency virus ("HIV"). The main targets of HIV are two different cells, the T4 lymphocyte and the macrophage. Once infected the T4 lymphocyte population generally begins to decline. Unlike the T4 lymphocytes, the macrophage is not killed by HIV infection but may actually serve as a reservoir for the virus. Gallo & Montagneir "AIDS in 1988", *Scientific American*, p. 25 (October 1988).

The early diagnosis of persons suffering from HIV infection generally involves using diagnostic tests to determine whether or not a person has antibodies to HIV. Early diagnosis is especially important in HIV infection as it enables the patient to receive optimal medical care from the earliest moments of the disease and to check further spread of the contagion. Redfield & Burke "HIV Infection: The Clinical Picture", *Scientific American*, p. 70.

European Patent application 219,368 A (corresponding to U.S. patent application Ser. No. 07/298,791) discloses certain monoclonal antibodies directed against proteins which form constituent parts of the "prosome". Prosomes are cellular particles described in Schmid et al "The prosome: an ubiquitous morphologically distinct RNP particle associated with repressed mRNPs and containing specific ScRNA and a characteristic set of proteins,", *The EMBO Journal*, 3(1), 29–34 (1984).

The prosome has been also variously called the "proteasome" or "mcp" (multicatalytic protease). European Patent application 0 345 750 A2 discloses a "polyfunctional protease", and antibodies thereto. The polyfunctional protease described in this application may be the prosome.

Since early 1990, mouse monoclonal antibodies against prosomal proteins have been commercially available from Organon Teknika nv of Turnhout, Belgium. The commercially available monoclonal antibodies have been ones directed against prosomal proteins p23K, p25K, p27K, p29K (p28K, p33K), p30/33K, and p31K and the anti-p21K ("prosome-like particle"). These antibodies are more thoroughly described in *Research Reagent News*, (January 1990) available from Organon Teknika nv.

In EP 219,368 A1, it is also disclosed that prosomes may be involved in many physiological processes related to the differentiation of cells and organisms, communication between cells, and to autoimmune disease. Also disclosed is that monoclonal antibodies directed against prosomes can be useful in the diagnosis of, for example, cancer.

In *Research Reagent News*, disclosed uses for the monoclonal antibodies against the prosomal proteins include the study of the molecular biology of prosomes, the distribution of specific types of prosomes in normal and pathological cells and tissues, messenger and other ribonucleoproteins.

No where is it described or suggested that any of these anti-prosomal proteins monoclonal antibodies might have any possible usefulness in the diagnosis of infectious diseases such as AIDS or HIV infection.

DISCLOSURE OF THE INVENTION

It has now been found that persons infected with HIV have cells (e.g. T4 and T8 lymphocytes as well as B4 cells) with different surface antigens than cells of persons not infected with the virus. Surprisingly, the presence of these surface antigens on the particular cells can be detected with certain labelled anti-prosomal protein monoclonal antibodies (i.e. monoclonal antibodies directed against prosomal proteins p23K, p25K, p27K, p29K (p28K, p33K), p30/33K, and p31K as well as monoclonal antibodies against p21K of the prosome-like particle).

The invention therefore includes a method of diagnosing HIV infection using these anti-prosomal protein and anti-prosome-like particle monoclonal antibodies, no matter what the source, in the diagnosis of HIV infection. The method can be used to determine whether T4 cells have been infected even before they are killed by HIV, thus enabling the method to be used as an early diagnostic tool for the diagnosis of HIV infection.

The method typically involves: obtaining body fluid containing cells capable of infection with HIV (e.g. blood) from a subject; separating, isolating or somehow identifying the particular cells in question present in the fluid; contacting the thus identified or isolated cells with an immunochemical agent containing one or more of the described monoclonal antibodies; and detecting the presence and relative amount of immune complexes formed between the cells and the monoclonal antibodies reactive therewith present in the blood. These results once obtained can be compared with a "norm" derived from a person not infected with HIV.

Monoclonal antibodies directed against the anti-prosomal proteins p27K and p33K can be raised by using certain polypeptides or fragments or derivatives thereof. These polypeptides have generally all or part of the primary structural conformation of the polypeptides shown in SEQ ID NO:1 or SEQ ID NO:3 and may be produced by the procaryotic or eucaryotic expression of an exogenous DNA source.

The invention therefore also includes the DNA sequence for use in securing expression in a procaryotic or eucaryotic host cell of a peptide product having at least part of the primary structure of the polypeptide depicted in SEQ ID NO:1 or SEQ ID NO:3. Generally such a DNA sequence will be selected from the group consisting of the DNA sequence set out in SEQ ID NO:1 or SEQ ID NO:3 or their complementary strands; DNA sequences which hybridize under stringent conditions to the protein coding regions of these DNA sequences or fragments thereof; and DNA sequences which, but for the degeneracy of the genetic code, would hybridize to those DNA sequences.

The invention thus includes the procaryotic or eucaryotic host cell transformed or transfected with such a DNA sequence, and the biologically functional circular plasmid or other DNA vector including such a DNA sequence.

The invention also includes the use of antibodies directed against prosomal proteins to analyze surface antigens present on a cell's surface for use, in example, phenotyping the cell. For this aspect of the invention the profiles presented in FIGS. 1–8 are used to identify an unknown white blood cell.

BRIEF DESCRIPTION OF THE FIGURES

FIG. 10 depicts the cDNA encoding another protein of the instant invention, and the amino acid sequence of that protein (the human p33K prosomal protein).

BEST MODE OF THE INVENTION

I. The Polypeptides

A polypeptide or peptide is a linear series of amino acids connected one to the other by peptide bonds between the α-amino and carboxy groups of adjacent amino acids. Preferred polypeptides for use in producing antibodies for use in the invention are depicted in SEQ ID NO:1 and SEQ ID NO:3.

The protein or polypeptide may be derived from whole prosomes which are found intracellularly, separately in the blood, and on cell membrane surfaces.

The preparation of the peptides or fragments thereof according to the invention may be by recombinant DNA methods or one of the known organic chemical methods for peptide synthesis.

Organic chemical methods are especially useful in the synthesis of smaller peptide fragments having the desired activity (e.g. the ability to be used to raise antibodies). Once the sequence of the fragment is known, the synthesis is rather straightforward for an ordinarily skilled peptide chemist. Organic chemical methods for peptide synthesis include coupling the required amino acids by means of a condensation reaction in either a homogenous phase or with the aid of a solid phase as disclosed by Merrifield. See, e.g. Merrifield, *J. Am. Chem. Society*, 85, 2149 (1963) and Wang, *J. Am. Chem. Soc.*, 95, 1328 (1974).

Different solid supports and different strategies are known for the solid phase synthesis see, e.g. Barany and Merrifield in *The peptides, Analysis, Synthesis, Biology*, Vol. 2, E. Gross and J. Meienhofer, eds., (Acad. Press, N.Y., 1980), Kneib-Cordonier and Mullen *Int. J. Peptide Protein Res.*, 30, 705–739 (1987) and Fields and Noble *Int. J. Peptide Protein Res.*, 35, 161–214 (1990).

Recombinant DNA methods involve the preparation of the desired peptide or fragment thereof by means of expressing recombinant polynucleotide with a polynucleotide sequence which codes for one or more of the peptides in question in a suitable microorganism as host. Generally the process involves introducing into a cloning vehicle (e.g. a plasmid, phage DNA, or other DNA sequence able to replicate in a host cell) a DNA sequence, such as that depicted in FIGS. 1 or 2; introducing said cloning vehicle into a suitable eucaryotic or procaryotic host cell; and culturing the host cell thus transformed. Typical host cells include bacteria such as *E. coli*, pseudomonas, and *Bacillus subtilis*. Eukaryotes such as various strains of yeast and mammalian cell lines are also very useful.

Once the peptides have been made, fragments useful in the invention can also be determined. Suitable immunochemically active peptide fragments can be found according to means of the method described in Patent Application WO 86/06487 to Geysen et al; Geysen et al, *Proc. Natl. Acad. Sci.*, (81) 3998–4002, (1984); and Geysen et al, *J. Immunol Meth.*, (102) 259–274 (1987) based on the "pepscan" method. In this method a series of overlapping peptides corresponding with partial sequences of the complete peptide under consideration are synthesized and their reactivity with the relevant antibodies is investigated.

Of course the fragments or peptides do not have to be exactly as depicted in SEQ ID NO:1 and SEQ ID NO:3. It is self-evident that one or more amino acids in the peptides may be substituted with other amino acids or amino acid analogues or derivatives so long as the immunochemical activity is not significantly adversely affected.

Furthermore functional derivatives of the peptides may also be used. Such functional derivatives include acid addition salts (such as hydrochloric, hydrobromic, fumaric, phosphoric, ascorbic, tartaric, citric, lactic, maleic, palmitic, and other well-known acids) of the peptides; amides of the peptides and especially the C-terminal amides; esters and especially C-terminal esters; and N-acyl derivatives, especially N-terminal acyl derivatives and in particular N-acetyl derivatives. All functional derivatives are considered "polypeptides", "peptides" and "peptide fragments" according to the invention.

Similarly, substitutions can be made in the nucleic acid sequences of SEQ ID NO:1 and SEQ ID NO:3. The degeneracy of the genetic code permits substitution of bases in a codon resulting in another codon, but still coding for the same amino acid. For example, the codon for the amino acid glutamic acid is both GAG and GAA. Consequently it is clear that for the expression of a polypeptide with the amino acid sequence shown in SEQ ID NO:1 or SEQ ID NO:3, or an antigenic fragment thereof, use can be made of a nucleic acid sequence with such an alternative codon composition or compositions different from the nucleic acid sequence shown in the figures.

Also included within the scope of the invention is a nucleic acid sequence which hybridizes under stringent conditions iwth a nucleic acid sequence shown in SEQ ID NO:1 or SEQ ID NO:3. These hybridizable nucleic acid sequences display substantial homology with a nucleic acid sequence shown in SEQ ID NO:1 or 3, or a fragment thereof, but may comprise nucleotide substitutions, mutations, insertions, deletions, inversions, etc. and encode a protein or polypeptide which is functionally equivalent to a prosomal protein or protein from a prosome-like particle. The resulting functionally equivalent protein, polypeptide or fragment will not be identical with a protein shown in SEQ ID NO:1, SEQ ID NO:3, or a fragment thereof, but will have corresponding antigenic properties.

II. Antibodies

Antibodies are preferably used to isolate or identify the cells of the patient to be studied (i.e. a patient's B4 cells, T4 cells, T8 cells, natural killer cells, T3 lymphocytes, or mixtures of these cells). Such antibodies are preferably monoclonal antibodies or monospecific polyclonal (e.g. affinity purified) antibodies, although polyclonal antibodies and antibody fragments may also be used. Monoclonal antibodies directed against the various cells are commercially available from companies such as Ortho Diagnostics or Coultronics of Paris, France, or may be made. For example, antibodies against natural killer cells are described in WO 8903396 (claiming priority from U.S. Ser. No. 109,730 filed on 16 Oct. 1987).

Antibodies against prosomal proteins for use in diagnostic kits and methods according to the invention are preferably monoclonal antibodies directed against the various prosomal proteins. Polyclonal antibodies and modified polyclonal antibodies may also be used however.

Monoclonal antibodies produced against the proteins can be produced by biologically pure cell lines of immortalized antibody-producing cells. Immortalized antibody producing cells can be obtained according to any of the various methods which are known in the art, and generally include the steps: 1) inducing suitable cells such as lymphocytes to produce specific antibodies (for example by injecting an immunogen, such as the polypeptide of SEQ ID NO:1 or SEQ ID NO:3), 2) immortalizing those cells, and 3) selecting clones out of these cells which produce antibodies of the desired specificity and affinity. For example, one method would be that of Kohler and Millstein, *Nature*, vol. 256, 495–497 (1975). This method comprises immunizing mice with the particular peptide (e.g. that of SEQ ID NO:1 or SEQ ID NO:3), isolating spleen cells and fusing these with mouse myeloma cells to obtain hybridomas. Of course animals other than mice could be used as well.

All of the specifically identified antibodies (i.e. those directed against the following proteins: p21K, p23K, p25K, p27K, p29K (p28K, p33K), p30/33K, and p31K) are commercially available from Organon Teknika nv. Deposits of cell lines producing monoclonal antibodies against the p27K and p31K have been made with the Collection Nationale de Cultures des Microorganismes of the Pasteur Institute under numbers I-588 and I-589. The antibodies may be likewise made as described in EP 219,368 A1 (corresponding to U.S. patent application Ser. No. 07/298,791).

Figure 1:
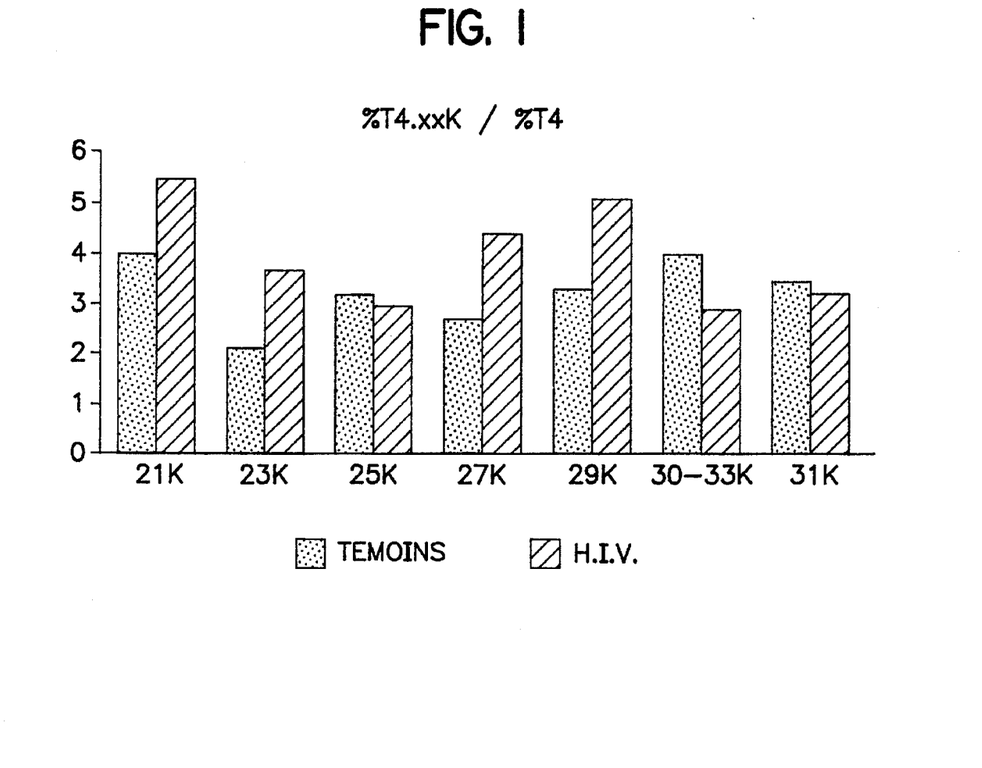
FIG. 1 is a graph depicting the percentage of T4 lymphocytes in blood reacting with various labelled anti-prosomal protein monoclonal antibodies in both non-HIV infected ("temoins") and HIV infected subjects.
Figure 2:
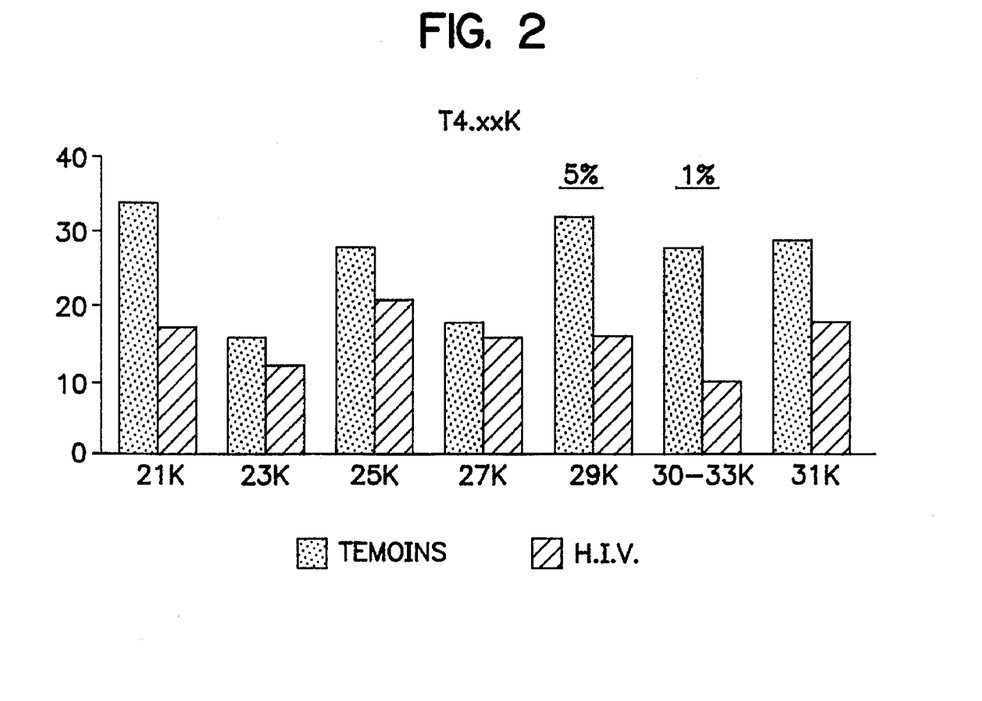
FIG. 2 is a graph depicting the number of T4 lymphocytes per cubic millimeter of subject blood reacting with various labelled anti-prosomal protein monoclonal antibodies in both non-HIV infected ("temoins") and HIV infected subjects.

For use in studying a subject's T4 cells to determine whether or not the subject is infected with HIV, anti-p27K antibody (p=0.01) and anti-p30–33K antibody (p=0.001), are preferred (FIGS. 1 and 2). However, anti-p29K (p=0.01) and anti-p23K antibody (p=0.001) may also be used (FIG. 1).

Figure 3:
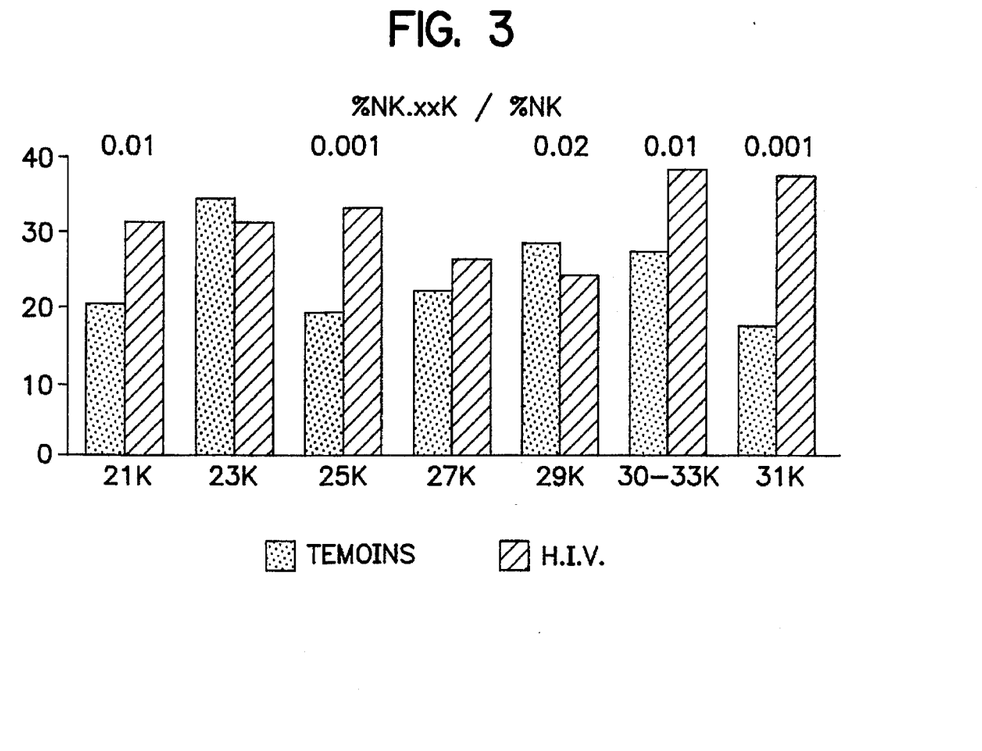
FIG. 3 is a graph depicting the percentage of natural killer cells ("NK") in blood reacting with various labelled anti-prosomal protein monoclonal antibodies in both non-HIV infected ("temoins") and HIV infected subjects.
Figure 4:
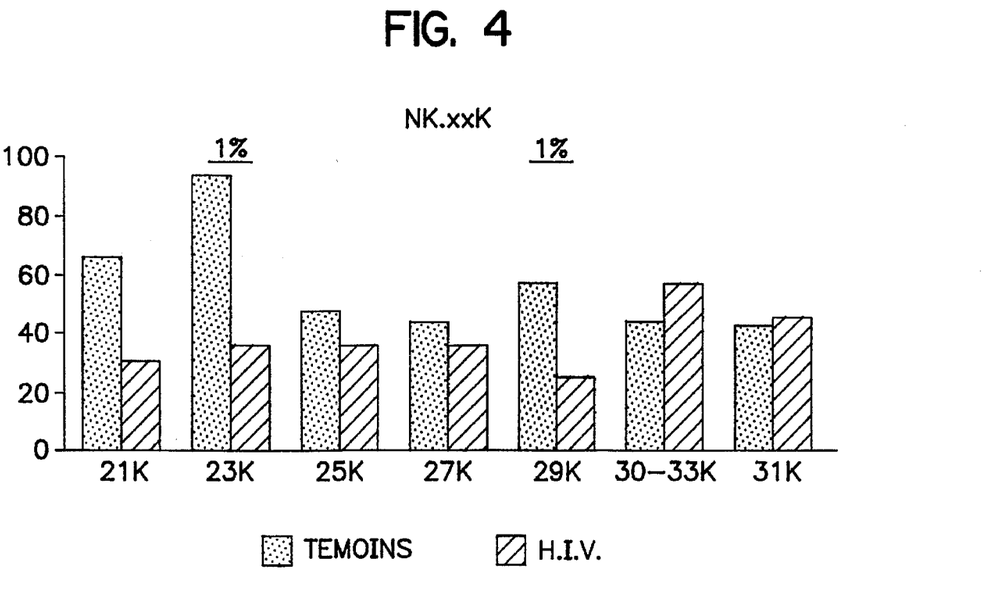
FIG. 4 is a graph depicting the number of NK per mm$^3$ of subject blood reacting with various labelled anti-prosomal protein monoclonal antibodies in both non-HIV infected ("temoins") and HIV infected subjects.

Monoclonal antibodies against any of the following antiprosomal proteins may be used to study a subject's natural killer cells to determine whether or not the subject has been infected with HIV: p25K, p29K (p28K, p33K), p30/33K, and p31K or the similar p21K (FIGS. 3 & 4).

Figure 5:
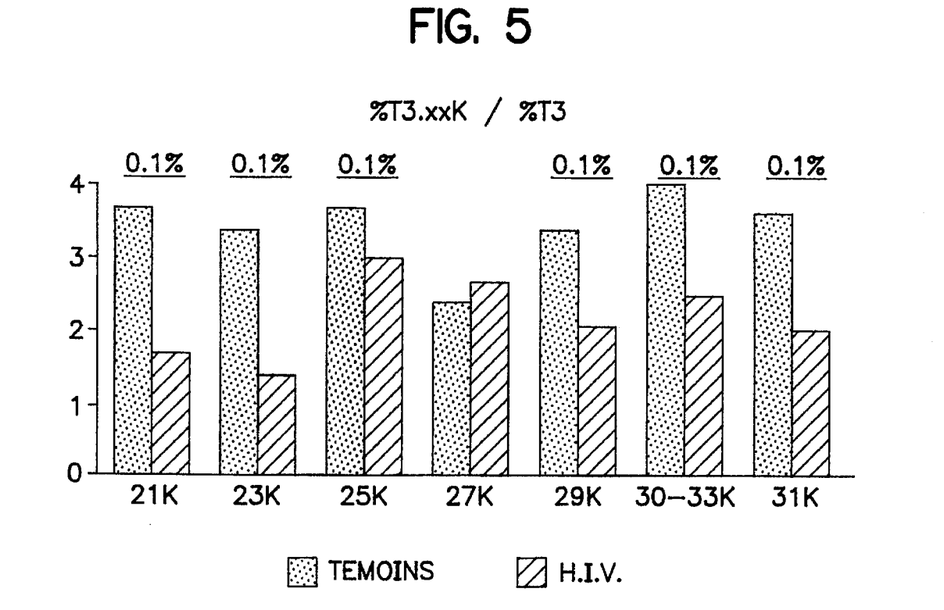
FIG. 5 is a graph depicting the percentage of T3 cells in blood reacting with various labelled anti-prosomal protein monoclonal antibodies in both non-HIV infected ("temoins") and HIV infected subjects.
Figure 6:
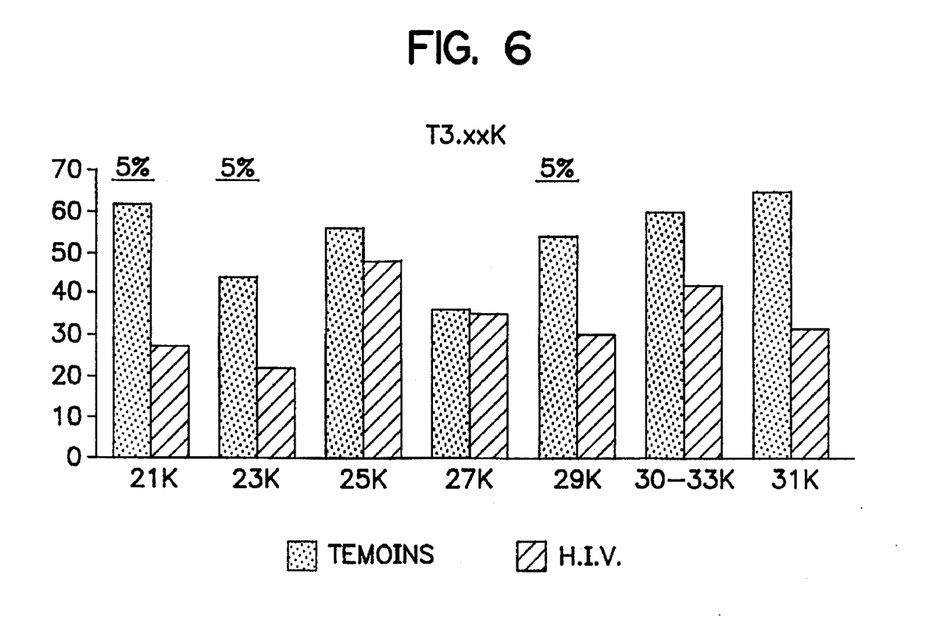
FIG. 6 is a graph depicting the number of T3 cells per mm$^3$ of subject blood reacting with various labelled anti-prosomal protein monoclonal antibodies in both non-HIV infected ("temoins") and HIV infected subjects.

Monoclonal antibodies against any of the following antiprosomal proteins may be used to study a subject's T3 lymphocytes to determine whether or not the subject has been infected with HIV: p23K, p25K, p29K (p28K, p33K), p30/33K, and p31K or the similar p21K (FIGS. 5 & 6). Preferred antibodies are those directed against the p21K, p23K, p29K, p30–33K, and the p31K.

Figure 7:
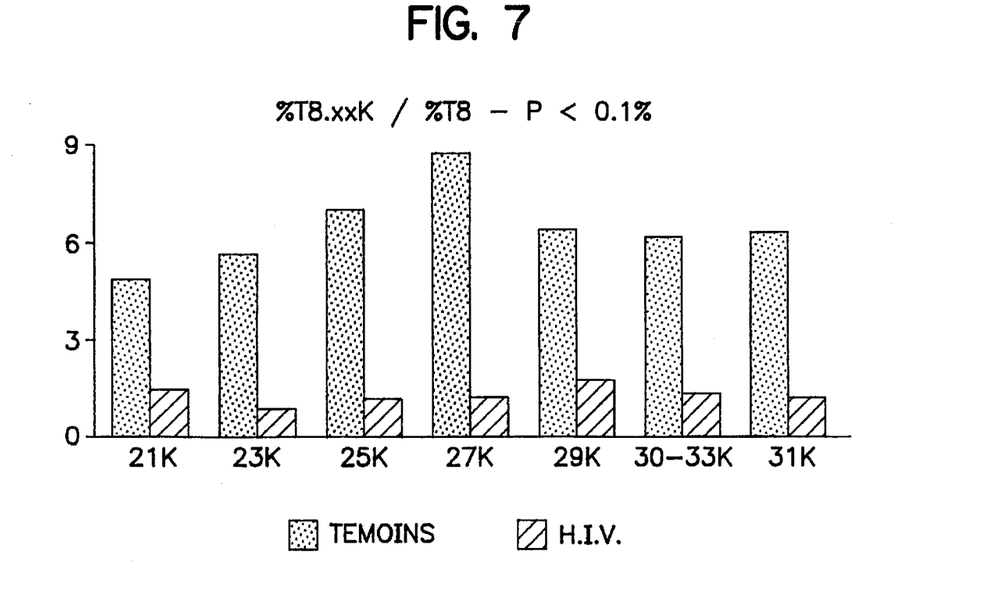
FIG. 7 is a graph depicting the percentage of T8 cells in blood reacting with various labelled anti-prosomal protein monoclonal antibodies in both non-HIV infected ("temoins") and HIV infected subjects.

Although monoclonal antibodies against any of the antiprosomal proteins (p23K, p25K, p27K, p29K (p28K, p33K), p30/33K, and p31K) or the similar anti-p21K (from a "prosome-like particle") may be used to study a subject's T8 cells to determine whether or not the subject is infected with HIV, anti-p27K antibody and anti-p30–33K antibody are preferred (FIG. 7).

Figure 8:
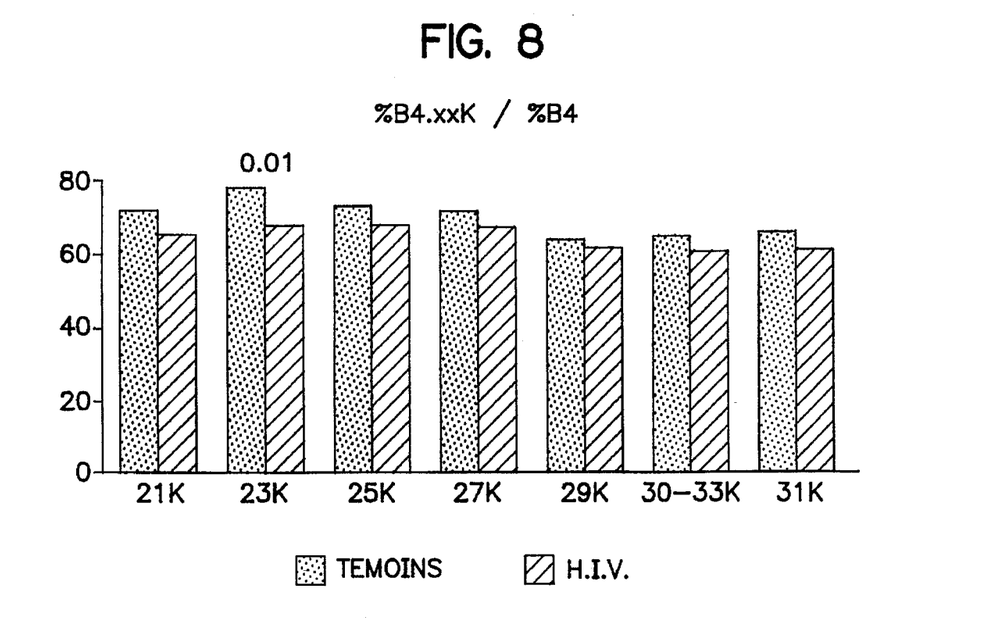
FIG. 8 is a graph depicting the percentage of B4 cells in blood reacting with various labelled anti-prosomal protein monoclonal antibodies in both non-HIV infected ("temoins") and HIV infected subjects.
Figure 9A:
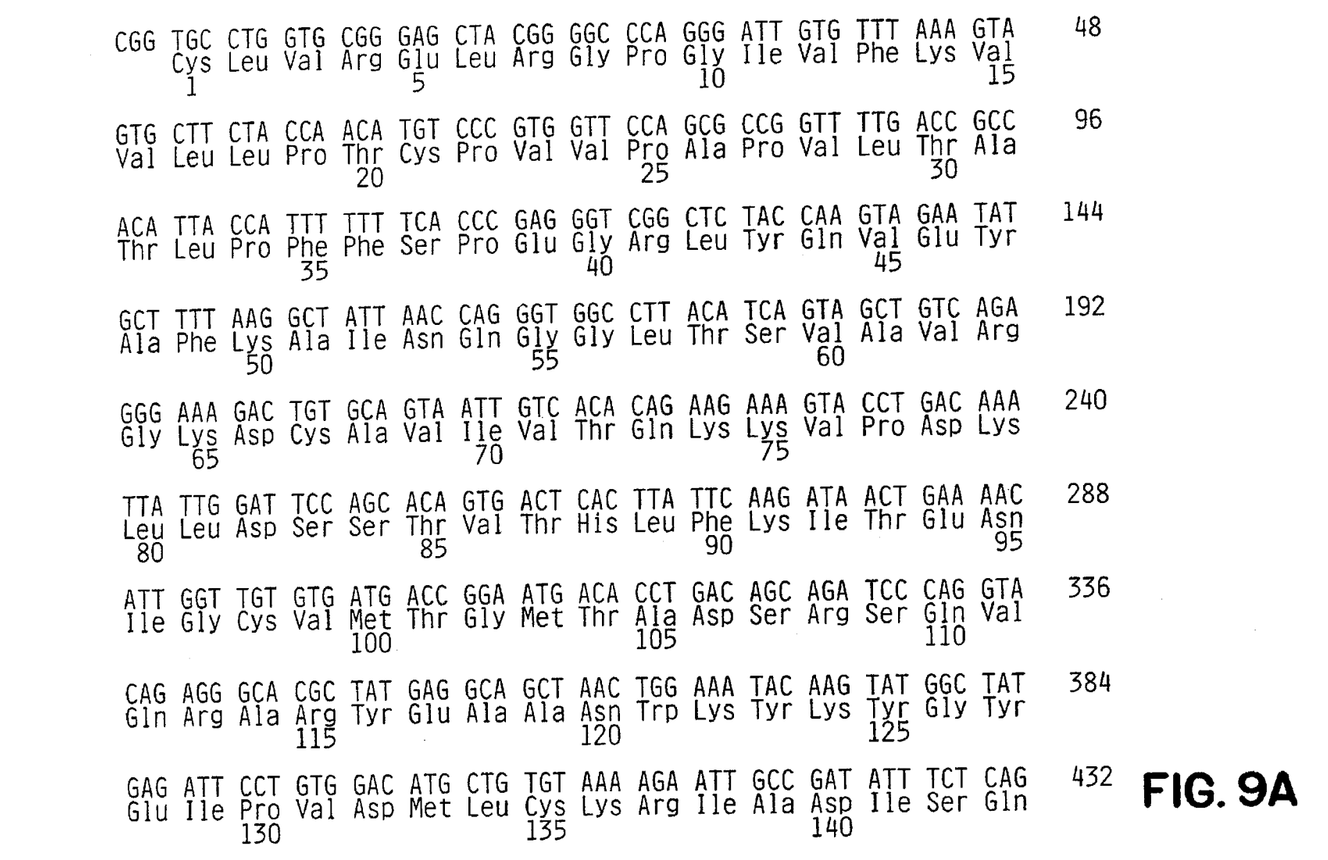
FIG. 9 depicts the cDNA encoding a protein of the instant invention, and the amino acid sequence of that protein (the human p27K prosomal protein).
Figure 9B:
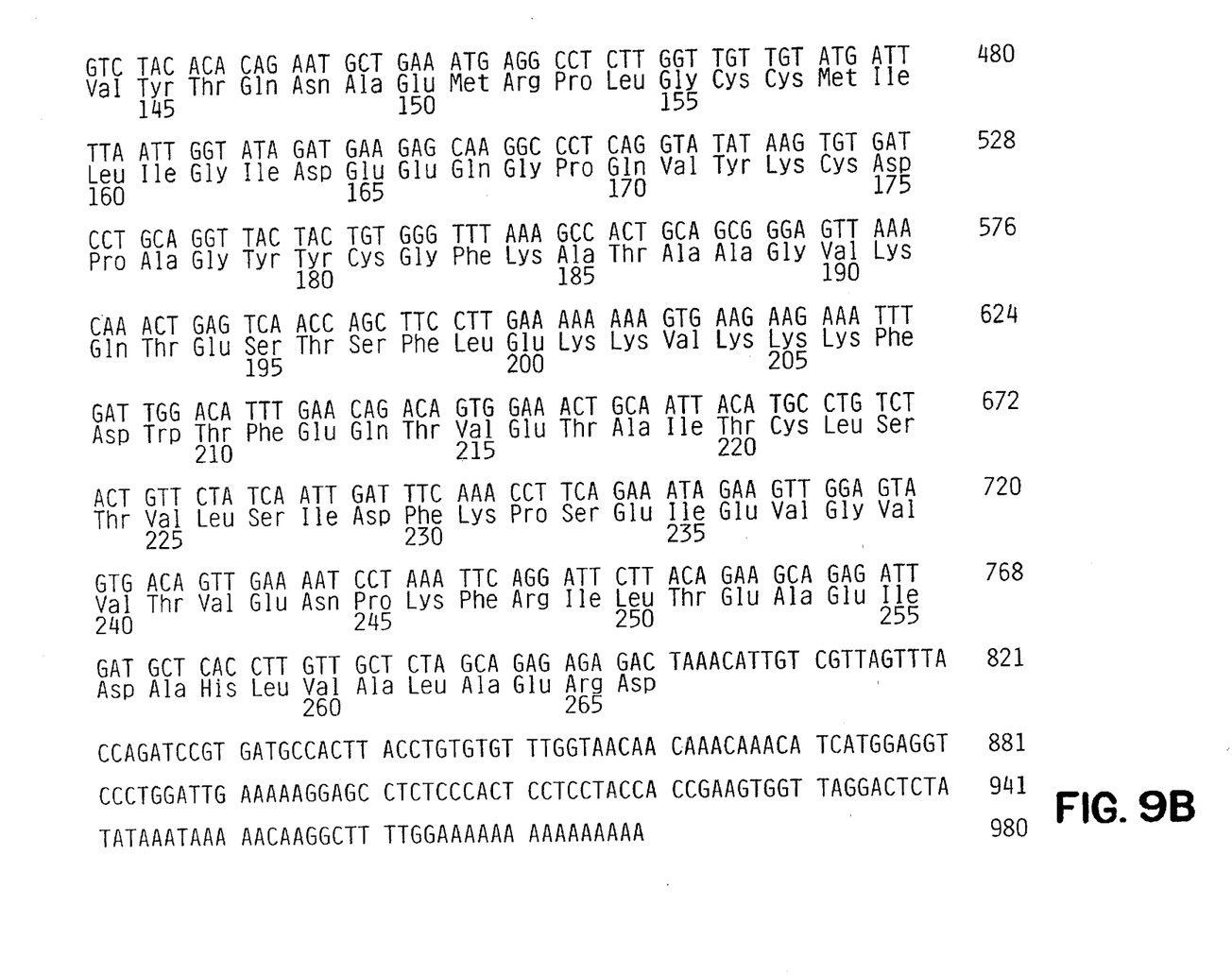

For use in studying a subject's B4 cells to determine whether or not the subject is infected with HIV, the anti-p23K antibody is preferred (FIG. 8).

III. Diagnostic Methods

In a preferred diagnostic method according to the invention, directly or indirectly labelled (e.g. with phycoerythrin) antibodies directed against the various cells (e.g. the T3 lymphocyte, T4 lymphocyte, T8 cell, B4 cell or natural killer cell) are used to identify or isolate these cells in a subject's blood containing the cells. The cell-antibody complexes are then incubated with antibodies directed against prosomal proteins also labelled, e.g with a fluorescent compound. The amount of cells thus labelled are measured or counted, and the measurement is compared with a norm or standard measurement.

Several devices can be used with the method.

As used herein an "immunochemical reagent" means that the antibodies displaying the appropriate selectivity have been bound to a suitable support or have been provided with a labelling substance. Supports typically used include the inner wall of a microtest well or a cuvette, a tube or capillary, a membrane filter, test strip, or the surface of a particle such as a latex particle, bead, erythrocyte, dye sol, metal (e.g. gold) sol or metal compound as sol particle. Labelling substances typically used include various radioactive isotopes, fluorescent compounds, enzymes, dye sols or metal compounds used as sol particles.

In one method of detecting the presence of HIV infection in a test fluid containing the described cells (e.g. a bodily fluid such as blood, lymph or plasma of a human thought to have been exposed to HIV), an immunochemical reagent of the invention is bought into contact with the test fluid. After which the presence of immune complexes formed between the antibodies and the surface antigens of the described cells in the test fluid is measured for the presence of an immunochemical reaction. The immunochemical reaction is preferably a sandwich reaction (using labelled antibody), an agglutination reaction (using also sols), a competition reaction, or an inhibition reaction.

In one type of immunoassay, antibodies directed against the cell or cells to be studied are attached to a solid phase, for example the inside of a test tube. The bodily fluid containing the desired cells are then added to the tube so as to bind with the antibody. To the tube coated with the antigen-antibody complex is added an immunological reagent containing a known amount of the appropriate anti-prosomal protein antibody or antibodies labelled with a fluorescent compound. The amount of fluorescence is thus measured, and compared with a norm.

Other diagnostic test kits are known to those skilled in the art which may be adapted for use in the instant invention. For example, immunological diagnostic test kits include radio-immunoassay or enzyme immunoactivity assay ("EIA") as described in U.S. Pat. Reissue No. 32,696 to Schuurs et al. A light scattering immunoassay system is disclosed in EP 0,254,430 A2 to Ortho Diagnostic Systems, Inc. (corresponding to U.S. Ser. No. 879,236 filed 26 Jun. 1986). Diagnostic test kits using two monoclonal antibodies of high binding affinity are described in U.S. Pat. Nos. 4,376,110 and 4,486,530 to Hybritech Inc.

A method of phenotyping a white blood cell comprises incubating the cell with labelled antibodies reactive with a prosomal protein; and analyzing the cell's surface by the means of the activity of the label for the presence of proteins reactive with the labeled antibody.

EXAMPLE I

Double Marking Immunology

The various cells to be analyzed were identified and isolated according to the following procedure. Monoclonal antibodies labelled with phycoerythrin ("PE") were introduced into 0.1 milliliters (ml) aliquots of blood and allowed to incubate for 10 minutes at room temperature. The monoclonal antibodies used in the various aliquots were anti-CD3 (T3-PE), anti-CD4 (T4-PE), anti-CD8 (T8-PE), anti-CD2 (11-PE), anti-CD19 (B4-PE), anti-NK (NK-PE). The red blood cells were lysed and fixed for passage by a flow cytometer QPREP (formic acid/formaldehyde—Coultronics France of Paris, France) to fix the cell membrane to ensure that it is not destroyed during preparation.

EXAMPLE II

Double Marking Immunology

Mouse serum was incubated for 4 to 5 hours at 4 degrees centigrade. It was washed once with concentrated PBS. It was then mixed with monoclonal antibodies directed against prosomal proteins, incubated, and allowed to cool to room temperature after 30 minutes. It was again washed with concentrated PBS one time. Goat anti-mouse fluorescein-isothiocyanate ("GAM-FITC") was then added in order to reveal the monoclonal antibodies against the prosomal proteins (30 minute incubation time at room temperature). It was again washed with concentrated PBS one time. It was then resuspended in 0.5 ml of concentrated PBS one time. Analysis of any fluorescence was made with CFM (flux cytometry).

EXAMPLE III

Using the procedures of EXAMPLEs I and II, the blood of 20 people who were HIV positive (2 of which were suffering from AIDS) was compared with the blood of a group of non-infected individuals. The results of comparing the subjects' (HIV-1) sera are graphically illustrated in FIGS. 1 through 8.

EXAMPLE IV

SEQ ID NO:1 depicts a 266 amino acid polypeptide along with the DNA coding therefor. The cDNA encoding this protein was isolated from a Hela cell cDNA expression library ((lambda)gt11), using a monoclonal antibody directed against the p27k prosomal protein (Organon Teknika). The insert was subcloned in pTZ18R plasmid vector for sequencing. The cDNA lacks approximately fifty nucleotides at the 5' end (as indicated by Northern blot analysis). The length of the DNA is 980 nucleotides, with a coding region of 798 nucleotides (266 amino acids).

EXAMPLE V

SEQ ID NO:3 depicts a 269 amino acid polypeptide along with the DNA coding therefor. The cDNA encoding this protein was isolated from a Hela cell cDNA expression library ((lambda)gt11) using a monoclonal antibody (62A32) directed against the p33K prosomal protein. The insert was subcloned in pTZ18R plasmid vector for sequencing. Sequencing of the insert in both directions revealed an open reading frame of 810 nucleotides and a full length sequence with a large 5' leader. The length of the DNA is 1264 nucleotides, with a coding region of 810 nucleotides (269 amino acids).

EXAMPLE VI

The protein of EXAMPLE IV (i.e. that of SEQ ID NO:1) is used to produce monoclonal antibodies against the p27K prosomal protein. The method comprises immunizing mice with the peptide, isolating spleen cells from the mice and fusing these with mouse myeloma cells to obtain hybridomas. The hybridomas are screened for those producing antibodies against the p27K protein.

EXAMPLE VII

Monoclonal antibodies against the polypeptide of EXAMPLE V (i.e. the protein of SEQ ID NO:3) are produced in a similar manner as that described in EXAMPLE VI.

What is claimed is:

1. A method useful in aiding in the diagnosis of human immunodeficiency virus infection, comprising:
   (a) identifying or isolating B4 cells from a blood sample using antibodies to B4 cells;
   (b) incubating the cells obtained in step (a) with a labeled monoclonal antibody to the prosomal protein p23K, and obtaining a quantitative determination of the amount or percentage of cells displaying the p23K protein on their surface; and
   (c) comparing the amount or percentage thus obtained with a standard from a person not infected with human immunodeficiency virus,
   whereby a decrease in the amount or percentage of cells displaying the p23K protein is indicative of HIV infection.

2. A method useful in aiding in the diagnosis of human immunodeficiency virus infection, comprising:
   (a) identifying or isolating T4 cells from a blood sample using antibodies to T4 cells;
   (b) incubating the cells obtained in step (a) with labeled monoclonal antibodies to the prosomal proteins, p23K, p27K, p29K and p30–33K, and obtaining a quantitative determination of the amount or percentage of cells displaying the p23K, p27K, p29K and p30–33K proteins on their surface; and
   (c) comparing the amount or percentage thus obtained with a standard from a person not infected with human immunodeficiency virus,
   whereby an increase in the amount or percentage of cells displaying the p23K, p27K and page proteins on their surface, and a decrease in the percentage of cells displaying p30–33K protein on their surface, is indicative of HIV infection.

3. A method useful in aiding in the diagnosis of human immunodeficiency virus infection, comprising:
   (a) identifying or isolating natural killer (NK) cells from a blood sample using antibodies to NK cells;
   (b) incubating the cells obtained in step (a) with labeled monoclonal antibodies to the prosomal proteins p21K, p25K, p29K, p30–33K and p31K, and obtaining a quantitative determination of the amount or percentage of cells displaying the p21K, p25K, p29K, p30–33K and p31K proteins on their surface; and
   (c) comparing the amount or percentage thus obtained with a standard from a person not infected with human immunodeficiency virus,
   whereby an increase in the percentage of cells displaying p21K, p25K, p30–33K and p31K proteins on their surface, and a decrease in the percentage of cells displaying p29K on their surface, is indicative of HIV infection.

4. A method useful in aiding in the diagnosis of human immunodeficiency virus infection, comprising:
   (a) identifying or isolating T3 cells from a blood sample using antibodies to T3 cells;
   (b) incubating the cells obtained in step (a) with labeled monoclonal antibodies to the prosomal proteins, p21K, p23K, p29K, p30–33K and p31K, and obtaining a quantitative determination of the amount or percentage of cells displaying the p21K, p23K, p29K, p30–33K and p31K proteins on their surface; and
   (c) comparing the amount or percentage thus obtained with a standard from a person not infected with human immunodeficiency virus,
   whereby a decrease in the percentage of cells displaying p21K, p23K, p28K, p30–33K and p31K proteins on their surface is indicative of HIV infection.

5. A method useful in aiding in the diagnosis of human immunodeficiency virus infection, comprising:
   (a) identifying or isolating T8 cells from a blood sample using antibodies to T8 cells;
   (b) incubating the cells obtained in step (a) with labeled monoclonal antibodies to the prosomal proteins, p27K and p30–33K, and obtaining a quantitative determination of the amount or percentage of cells displaying the p27K and p30–33K proteins on their surface; and
   (c) comparing the amount or percentage thus obtained with a standard from a person not infected with human immunodeficiency virus, whereby a decrease in the percentage of cells displaying p27K and p30–33K proteins on their surface is indicative of HIV infection.

6. A diagnostic test kit for use in aiding in the diagnosis of a human immunodeficiency virus infection comprising: antibodies directed against cells selected from the group consisting of B4 cells, T4 cells, T8 cells, natural killer cells, T3 lymphocytes, and mixtures of these cells associated with a solid surface; and a diagnostic fluid containing labeled antibodies against prosomal proteins selected from the group consisting of p21K, p23K, p25K, p27K, p29K, p30–33K, and p31K.

* * * * *

UNITED STATES PATENT AND TRADEMARK OFFICE
CERTIFICATE OF CORRECTION

PATENT NO. : 5,635,345
DATED : June 3, 1997
INVENTOR(S) : Scherrer et al.

It is certified that error appears in the above-indentified patent and that said Letters Patent is hereby corrected as shown below:

On title page, item [73]
Please correct the following:
In the "Assignee" section on the title page, delete "Akzo Nobel N.V., Arnhem, Netherlands" and replace with -- Pro Soma S.A.R.L., Paris, France --

Signed and Sealed this

Twenty-ninth Day of December, 1998

Attest:

BRUCE LEHMAN

*Attesting Officer*   *Commissioner of Patents and Trademarks*

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 980 nucleotides
        ( B ) TYPE: nucleotide
        ( C ) STRANDEDNESS: double
        ( D ) TOPOLOGY: linear     ( i i ) MOLECULE TYPE: cDNA     ( i i i ) HYPOTHETICAL: no     ( v i ) ORIGINAL SOURCE:
        ( A ) ORGANISM: human     ( v i i ) IMMEDIATE SOURCE:
        ( A ) LIBRARY: Hela cell cDNA expression library (lambda)gt11

( i x ) FEATURE:

( B ) LOCATION: 4..804

( x i ) SEQUENCE DESCRIPTION: SEQ ID NO:1:

| | | | | | | | | | | | | | | | | |
|---|---|---|---|---|---|---|---|---|---|---|---|---|---|---|---|---|
| CGG | TGC | CTG | GTG | CGG | GAG | CTA | CGG | GGC | CCA | GGG | ATT | GTG | TTT | AAA | GTA | 48 |
| | Cys | Leu | Val | Arg | Glu | Leu | Arg | Gly | Pro | Gly | Ile | Val | Phe | Lys | Val | |
| | 1 | | | | 5 | | | | | 10 | | | | | 15 | |
| GTG | CTT | CTA | CCA | ACA | TGT | CCC | GTG | GTT | CCA | GCG | CCG | GTT | TTG | ACC | GCC | 96 |
| Val | Leu | Leu | Pro | Thr | Cys | Pro | Val | Val | Pro | Ala | Pro | Val | Leu | Thr | Ala | |
| | | | | 20 | | | | | 25 | | | | | 30 | | |
| ACA | TTA | CCA | TTT | TTT | TCA | CCC | GAG | GGT | CGG | CTC | TAC | CAA | GTA | GAA | TAT | 144 |
| Thr | Leu | Pro | Phe | Phe | Ser | Pro | Glu | Gly | Arg | Leu | Tyr | Gln | Val | Glu | Tyr | |
| | | | | 35 | | | | | 40 | | | | | 45 | | |
| GCT | TTT | AAG | GCT | ATT | AAC | CAG | GGT | GGC | CTT | ACA | TCA | GTA | GCT | GTC | AGA | 192 |
| Ala | Phe | Lys | Ala | Ile | Asn | Gln | Gly | Gly | Leu | Thr | Ser | Val | Ala | Val | Arg | |
| | | 50 | | | | | 55 | | | | | 60 | | | | |
| GGG | AAA | GAC | TGT | GCA | GTA | ATT | GTC | ACA | CAG | AAG | AAA | GTA | CCT | GAC | AAA | 240 |
| Gly | Lys | Asp | Cys | Ala | Val | Ile | Val | Thr | Gln | Lys | Lys | Val | Pro | Asp | Lys | |
| | 65 | | | | | 70 | | | | | 75 | | | | | |
| TTA | TTG | GAT | TCC | AGC | ACA | GTG | ACT | CAC | TTA | TTC | AAG | ATA | ACT | GAA | AAC | 288 |
| Leu | Leu | Asp | Ser | Ser | Thr | Val | Thr | His | Leu | Phe | Lys | Ile | Thr | Glu | Asn | |
| 80 | | | | | 85 | | | | | 90 | | | | | 95 | |
| ATT | GGT | TGT | GTG | ATG | ACC | GGA | ATG | ACA | GCT | GAC | AGC | AGA | TCC | CAG | GTA | 336 |
| Ile | Gly | Cys | Val | Met | Thr | Gly | Met | Thr | Ala | Asp | Ser | Arg | Ser | Gln | Val | |
| | | | | 100 | | | | | 105 | | | | | 110 | | |
| CAG | AGG | GCA | CGC | TAT | GAG | GCA | GCT | AAC | TGG | AAA | TAC | AAG | TAT | GGC | TAT | 384 |
| Gln | Arg | Ala | Arg | Tyr | Glu | Ala | Ala | Asn | Trp | Lys | Tyr | Lys | Tyr | Gly | Tyr | |
| | | | 115 | | | | | 120 | | | | | 125 | | | |
| GAG | ATT | CCT | GTG | GAC | ATG | CTG | TGT | AAA | AGA | ATT | GCC | GAT | ATT | TCT | CAG | 432 |
| Glu | Ile | Pro | Val | Asp | Met | Leu | Cys | Lys | Arg | Ile | Ala | Asp | Ile | Ser | Gln | |
| | | 130 | | | | | 135 | | | | | 140 | | | | |
| GTC | TAC | ACA | CAG | AAT | GCT | GAA | ATG | AGG | CCT | CTT | GGT | TGT | TGT | ATG | ATT | 480 |
| Val | Tyr | Thr | Gln | Asn | Ala | Glu | Met | Arg | Pro | Leu | Gly | Cys | Cys | Met | Ile | |
| | 145 | | | | | 150 | | | | | 155 | | | | | |
| TTA | ATT | GGT | ATA | GAT | GAA | GAG | CAA | GGC | CCT | CAG | GTA | TAT | AAG | TGT | GAT | 528 |
| Leu | Ile | Gly | Ile | Asp | Glu | Glu | Gln | Gly | Pro | Gln | Val | Tyr | Lys | Cys | Asp | |
| 160 | | | | | 165 | | | | | 170 | | | | | 175 | |
| CCT | GCA | GGT | TAC | TAC | TGT | GGG | TTT | AAA | GCC | ACT | GCA | GCG | GGA | GTT | AAA | 576 |
| Pro | Ala | Gly | Tyr | Tyr | Cys | Gly | Phe | Lys | Ala | Thr | Ala | Ala | Gly | Val | Lys | |
| | | | | 180 | | | | | 185 | | | | | 190 | | |
| CAA | ACT | GAG | TCA | ACC | AGC | TTC | CTT | GAA | AAA | AAA | GTG | AAG | AAG | AAA | TTT | 624 |
| Gln | Thr | Glu | Ser | Thr | Ser | Phe | Leu | Glu | Lys | Lys | Val | Lys | Lys | Lys | Phe | |
| | | | 195 | | | | | 200 | | | | | 205 | | | |
| GAT | TGG | ACA | TTT | GAA | CAG | ACA | GTG | GAA | ACT | GCA | ATT | ACA | TGC | CTG | TCT | 672 |
| Asp | Trp | Thr | Phe | Glu | Gln | Thr | Val | Glu | Thr | Ala | Ile | Thr | Cys | Leu | Ser | |
| | | 210 | | | | | 215 | | | | | 220 | | | | |
| ACT | GTT | CTA | TCA | ATT | GAT | TTC | AAA | CCT | TCA | GAA | ATA | GAA | GTT | GGA | GTA | 720 |
| Thr | Val | Leu | Ser | Ile | Asp | Phe | Lys | Pro | Ser | Glu | Ile | Glu | Val | Gly | Val | |
| | 225 | | | | | 230 | | | | | 235 | | | | | |
| GTG | ACA | GTT | GAA | AAT | CCT | AAA | TTC | AGG | ATT | CTT | ACA | GAA | GCA | GAG | ATT | 768 |
| Val | Thr | Val | Glu | Asn | Pro | Lys | Phe | Arg | Ile | Leu | Thr | Glu | Ala | Glu | Ile | |
| 240 | | | | | 245 | | | | | 250 | | | | | 255 | |
| GAT | GCT | CAC | CTT | GTT | GCT | CTA | GCA | GAG | AGA | GAC | TAAACATTGT CGTTAGTTTA | | | | 821 |
| Asp | Ala | His | Leu | Val | Ala | Leu | Ala | Glu | Arg | Asp | | | | | | |
| | | | | 260 | | | | | 265 | | | | | | | |

CCAGATCCGT GATGCCACTT ACCTGTGTGT TTGGTAACAA CAAACAAACA TCATGGAGGT 881

CCCTGGATTG AAAAAGGAGC CTCTCCCACT CCTCCTACCA CCGAAGTGGT TAGGACTCTA 941

TATAAATAAA AACAAGGCTT TTGGAAAAAA AAAAAAAAA 980

( 2 ) INFORMATION FOR SEQ ID NO:2:

(i) SEQUENCE CHARACTERISTICS:
    (A) LENGTH: 266 amino acids
    (B) TYPE: amino acid
    (C) TOPOLOGY: linear (ii) MOLECULE TYPE: protein (vi) ORIGINAL SOURCE:
    (A) ORGANISM: human (xi) SEQUENCE DESCRIPTION: SEQ ID NO:2:

```
Cys Leu Val Arg Glu Leu Arg Gly Pro Gly Ile Val Phe Lys Val
 1               5                  10                  15
Val Leu Leu Pro Thr Cys Pro Val Val Pro Ala Pro Val Leu Thr Ala
                20                  25                  30
Thr Leu Pro Phe Phe Ser Pro Glu Gly Arg Leu Tyr Gln Val Glu Tyr
                35                  40                  45
Ala Phe Lys Ala Ile Asn Gln Gly Gly Leu Thr Ser Val Ala Val Arg
                50                  55                  60
Gly Lys Asp Cys Ala Val Ile Val Thr Gln Lys Lys Val Pro Asp Lys
        65                  70                  75
Leu Leu Asp Ser Ser Thr Val Thr His Leu Phe Lys Ile Thr Glu Asn
 80                  85                  90                  95
Ile Gly Cys Val Met Thr Gly Met Thr Ala Asp Ser Arg Ser Gln Val
                    100                 105                 110
Gln Arg Ala Arg Tyr Glu Ala Ala Asn Trp Lys Tyr Lys Tyr Gly Tyr
                115                 120                 125
Glu Ile Pro Val Asp Met Leu Cys Lys Arg Ile Ala Asp Ile Ser Gln
            130                 135                 140
Val Tyr Thr Gln Asn Ala Glu Met Arg Pro Leu Gly Cys Cys Met Ile
    145                 150                 155
Leu Ile Gly Ile Asp Glu Glu Gln Gly Pro Gln Val Tyr Lys Cys Asp
160                 165                 170                 175
Pro Ala Gly Tyr Tyr Cys Gly Phe Lys Ala Thr Ala Ala Gly Val Lys
                    180                 185                 190
Gln Thr Glu Ser Thr Ser Phe Leu Glu Lys Lys Val Lys Lys Lys Phe
                195                 200                 205
Asp Trp Thr Phe Glu Gln Thr Val Glu Thr Ala Ile Thr Cys Leu Ser
            210                 215                 220
Thr Val Leu Ser Ile Asp Phe Lys Pro Ser Glu Ile Glu Val Gly Val
    225                 230                 235
Val Thr Val Glu Asn Pro Lys Phe Arg Ile Leu Thr Glu Ala Glu Ile
240                 245                 250                 255
Asp Ala His Leu Val Ala Leu Ala Glu Arg Asp
                260                 265
```

(2) INFORMATION FOR SEQ ID NO:3:

(i) SEQUENCE CHARACTERISTICS:
        (A) LENGTH: 1264 base pairs
        (B) TYPE: nucleic acid
        (C) STRANDEDNESS: double
        (D) TOPOLOGY: linear     (ii) MOLECULE TYPE: cDNA     (vi) ORIGINAL SOURCE:
        (A) ORGANISM: human     (vii) IMMEDIATE SOURCE:
        (A) LIBRARY: Hela cell cDNA expression library (lambda)gt11

( i x ) FEATURE:
    ( B ) LOCATION: 328..1137

( x i ) SEQUENCE DESCRIPTION: SEQ ID NO:3:

```
CGCGAGCCGG GACCACGCCG ACCCAGCGTG CCCAGGCCGA GGAAAGCGCG GCGGCGGCAG   60

TCCGAAGACC CACCGGACTG AAAGAGAAGG ACGAGGTCAT CTTCGGACGG GAGGGGCAAG  120

CCAGCCATCC TGGGACCCCA GGCGTGCAGG TTCTCTTTGA GGGTATTCCA CCCTGCAAAA  180

AGCATGTATT CATGGTCAGC TCTCAGCAAG GCCAGTAGCA GAGTGGTAAA GGCCTTGGCC  240

CTCCAAGGCT GGGAAAAGAC AATGACAAGT CAAATCCAGA CCTATGTTGG ATGTTGGTCT  300

ACTAGGTGAC TGTCTCCTGG AAATGTT ATG CAG CTC AGC AAG GTG AAG TTT CGA  354
                              Met Gln Leu Ser Lys Val Lys Phe Arg
                                1               5
```

| AAT | CAG | TAT | GAC | AAT | GAT | GTC | ACT | GTT | TGG | ACC | GCC | CAG | GGC | AGG | ATT | 402 |
|-----|-----|-----|-----|-----|-----|-----|-----|-----|-----|-----|-----|-----|-----|-----|-----|-----|
| Asn | Gln | Tyr | Asp | Asn | Asp | Val | Thr | Val | Trp | Thr | Ala | Gln | Gly | Arg | Ile | |
| 10 | | | | 15 | | | | | 20 | | | | | | 25 | |

| CAT | CAA | ATT | GAA | TAT | GCA | ATG | GAA | GCT | GTT | AAA | CAA | GGT | TCA | GCC | ACA | 450 |
|-----|-----|-----|-----|-----|-----|-----|-----|-----|-----|-----|-----|-----|-----|-----|-----|-----|
| His | Gln | Ile | Glu | Tyr | Ala | Met | Glu | Ala | Val | Lys | Gln | Gly | Ser | Ala | Thr | |
| | | | | 30 | | | | | 35 | | | | | 40 | | |

| GTT | GGT | CTG | AAA | TCA | AAA | ACT | CAT | GCA | GTT | TTG | GTT | GCA | TTG | AAA | AGG | 498 |
|-----|-----|-----|-----|-----|-----|-----|-----|-----|-----|-----|-----|-----|-----|-----|-----|-----|
| Val | Gly | Leu | Lys | Ser | Lys | Thr | His | Ala | Val | Leu | Val | Ala | Leu | Lys | Arg | |
| | | | 45 | | | | | 50 | | | | | 55 | | | |

| GCG | CAA | TCA | GAG | CTT | GCA | GCT | CAT | CAG | AAA | AAA | ATT | CTC | CAT | GTT | GAC | 546 |
|-----|-----|-----|-----|-----|-----|-----|-----|-----|-----|-----|-----|-----|-----|-----|-----|-----|
| Ala | Gln | Ser | Glu | Leu | Ala | Ala | His | Gln | Lys | Lys | Ile | Leu | His | Val | Asp | |
| | | 60 | | | | | 65 | | | | | 70 | | | | |

| AAC | CAT | ATT | GGT | ATC | TCA | ATT | GCG | GGG | CTT | ACT | GCT | GAT | GCT | AGA | CTG | 594 |
|-----|-----|-----|-----|-----|-----|-----|-----|-----|-----|-----|-----|-----|-----|-----|-----|-----|
| Asn | His | Ile | Gly | Ile | Ser | Ile | Ala | Gly | Leu | Thr | Ala | Asp | Ala | Arg | Leu | |
| | 75 | | | | 80 | | | | | 85 | | | | | | |

| TTA | TGT | AAT | TTT | ATG | CGT | CAG | GAG | TGT | TTG | GAT | TCC | AGA | TTT | GTA | TTC | 642 |
|-----|-----|-----|-----|-----|-----|-----|-----|-----|-----|-----|-----|-----|-----|-----|-----|-----|
| Leu | Cys | Asn | Phe | Met | Arg | Gln | Glu | Cys | Leu | Asp | Ser | Arg | Phe | Val | Phe | |
| 90 | | | | 95 | | | | | 100 | | | | | 105 | | |

| GAT | AGA | CCA | CTG | CCT | GTG | TCT | CGT | CTT | GTA | TCT | CTA | ATT | GGA | AGC | AAG | 690 |
|-----|-----|-----|-----|-----|-----|-----|-----|-----|-----|-----|-----|-----|-----|-----|-----|-----|
| Asp | Arg | Pro | Leu | Pro | Val | Ser | Arg | Leu | Val | Ser | Leu | Ile | Gly | Ser | Lys | |
| | | | | 110 | | | | | 115 | | | | | 120 | | |

| ACC | CAG | ATA | CCA | ACA | CAA | CGA | TAT | GGC | CGG | AGA | CCA | TAT | GGT | GTT | GGT | 738 |
|-----|-----|-----|-----|-----|-----|-----|-----|-----|-----|-----|-----|-----|-----|-----|-----|-----|
| Thr | Gln | Ile | Pro | Thr | Gln | Arg | Tyr | Gly | Arg | Arg | Pro | Tyr | Gly | Val | Gly | |
| | | | 125 | | | | | 130 | | | | | 135 | | | |

| CTC | CTT | ATT | GCT | GGT | TAT | GAT | GAT | ATG | GGC | CCT | CAC | ATT | TTC | CAA | ACC | 786 |
|-----|-----|-----|-----|-----|-----|-----|-----|-----|-----|-----|-----|-----|-----|-----|-----|-----|
| Leu | Leu | Ile | Ala | Gly | Tyr | Asp | Asp | Met | Gly | Pro | His | Ile | Phe | Gln | Thr | |
| | | | 140 | | | | | 145 | | | | | 150 | | | |

| TGT | CCA | TCT | GCT | AAC | TAT | TTT | GAC | TGC | AGA | GCC | ATG | TCC | ATT | GGA | GCC | 834 |
|-----|-----|-----|-----|-----|-----|-----|-----|-----|-----|-----|-----|-----|-----|-----|-----|-----|
| Cys | Pro | Ser | Ala | Asn | Tyr | Phe | Asp | Cys | Arg | Ala | Met | Ser | Ile | Gly | Ala | |
| | 155 | | | | | 160 | | | | | 165 | | | | | |

| CGT | TCC | CAA | TCA | GCT | CGT | ACT | TAC | TTG | GAG | AGA | CAT | ATG | TCT | GAA | TTT | 882 |
|-----|-----|-----|-----|-----|-----|-----|-----|-----|-----|-----|-----|-----|-----|-----|-----|-----|
| Arg | Ser | Gln | Ser | Ala | Arg | Thr | Tyr | Leu | Glu | Arg | His | Met | Ser | Glu | Phe | |
| 170 | | | | | 175 | | | | | 180 | | | | | 185 | |

| ATG | GAG | TGT | AAT | TTA | AAT | GAA | CTA | GTT | AAA | CAT | GGT | CTG | CGT | GCC | TTA | 930 |
|-----|-----|-----|-----|-----|-----|-----|-----|-----|-----|-----|-----|-----|-----|-----|-----|-----|
| Met | Glu | Cys | Asn | Leu | Asn | Glu | Leu | Val | Lys | His | Gly | Leu | Arg | Ala | Leu | |
| | | | | 190 | | | | | 195 | | | | | 200 | | |

| AGA | GAG | ACG | CTT | CCT | GCA | GAA | CAG | GAC | CTG | ACT | ACA | AAG | AAT | GTT | TCC | 978 |
|-----|-----|-----|-----|-----|-----|-----|-----|-----|-----|-----|-----|-----|-----|-----|-----|-----|
| Arg | Glu | Thr | Leu | Pro | Ala | Glu | Gln | Asp | Leu | Thr | Thr | Lys | Asn | Val | Ser | |
| | | | 205 | | | | | 210 | | | | | 215 | | | |

| ATT | GGA | ATT | GTT | GGT | AAA | GAC | TTG | GAG | TTT | ACA | ATC | TAT | GAT | GAT | GAT | 1026 |
|-----|-----|-----|-----|-----|-----|-----|-----|-----|-----|-----|-----|-----|-----|-----|-----|------|
| Ile | Gly | Ile | Val | Gly | Lys | Asp | Leu | Glu | Phe | Thr | Ile | Tyr | Asp | Asp | Asp | |
| | | | 220 | | | | | 225 | | | | | 230 | | | |

| GAT | GTG | TCT | CCA | TTC | CTG | GAA | GGT | CTT | GAA | GAA | AGA | CCA | CAG | AGA | AAG | 1074 |
|-----|-----|-----|-----|-----|-----|-----|-----|-----|-----|-----|-----|-----|-----|-----|-----|------|
| Asp | Val | Ser | Pro | Phe | Leu | Glu | Gly | Leu | Glu | Glu | Arg | Pro | Gln | Arg | Lys | |
| | | 235 | | | | | 240 | | | | | 245 | | | | |

```
GCA CAG CCT GCT CAA CCT GCT GAT GAA CCT GCA GAA AAG GCT GAT GAA    1122
Ala Gln Pro Ala Gln Pro Ala Asp Glu Pro Ala Glu Lys Ala Asp Glu
250                 255                 260                 265

CCA ATG GAA CAT TAAGTGATAA GCCAGTCTAT ATATGTATTA TCAAATATGT        1174
Pro Met Glu His

AAGAATACAG GCACCACATA CTGATGACAA TAATCTATAC TTTAACCAAA AGTTGCAGAG  1234

TGGTGGAATG CTATTTTTTA GGAATCAGTC                                   1264
```

( 2 ) INFORMATION FOR SEQ ID NO:4:

( i ) SEQUENCE CHARACTERISTICS:
        ( A ) LENGTH: 269 amino acids
        ( B ) TYPE: amino acid
        ( C ) TOPOLOGY: linear     ( i i ) MOLECULE TYPE: protein     ( v i ) ORIGINAL SOURCE:
        ( A ) ORGANISM: human     ( x i ) SEQUENCE DESCRIPTION: SEQ ID NO:4:

```
                            Met Gln Leu Ser Lys Val Lys Phe Arg
                             1               5
Asn Gln Tyr Asp Asn Asp Val Thr Val Trp Thr Ala Gln Gly Arg Ile
 10                  15                  20                  25
His Gln Ile Glu Tyr Ala Met Glu Ala Val Lys Gln Gly Ser Ala Thr
                     30                  35                  40
Val Gly Leu Lys Ser Lys Thr His Ala Val Leu Val Ala Leu Lys Arg
                 45                  50                  55
Ala Gln Ser Glu Leu Ala Ala His Gln Lys Lys Ile Leu His Val Asp
             60                  65                  70
Asn His Ile Gly Ile Ser Ile Ala Gly Leu Thr Ala Asp Ala Arg Leu
 75                  80                  85
Leu Cys Asn Phe Met Arg Gln Glu Cys Leu Asp Ser Arg Phe Val Phe
 90                  95                 100                 105
Asp Arg Pro Leu Pro Val Ser Arg Leu Val Ser Leu Ile Gly Ser Lys
                110                 115                 120
Thr Gln Ile Pro Thr Gln Arg Tyr Gly Arg Arg Pro Tyr Gly Val Gly
             125                 130                 135
Leu Leu Ile Ala Gly Tyr Asp Asp Met Gly Pro His Ile Phe Gln Thr
             140                 145                 150
Cys Pro Ser Ala Asn Tyr Phe Asp Cys Arg Ala Met Ser Ile Gly Ala
     155                 160                 165
Arg Ser Gln Ser Ala Arg Thr Tyr Leu Glu Arg His Met Ser Glu Phe
170                 175                 180                 185
Met Glu Cys Asn Leu Asn Glu Leu Val Lys His Gly Leu Arg Ala Leu
                190                 195                 200
Arg Glu Thr Leu Pro Ala Glu Gln Asp Leu Thr Thr Lys Asn Val Ser
             205                 210                 215
Ile Gly Ile Val Gly Lys Asp Leu Glu Phe Thr Ile Tyr Asp Asp Asp
             220                 225                 230
Asp Val Ser Pro Phe Leu Glu Gly Leu Glu Glu Arg Pro Gln Arg Lys
     235                 240                 245
Ala Gln Pro Ala Gln Pro Ala Asp Glu Pro Ala Glu Lys Ala Asp Glu
250                 255                 260                 265
Pro Met Glu His
```